United States Patent [19]

Diesso

[11] Patent Number: 5,112,225
[45] Date of Patent: May 12, 1992

[54] CUSTOM DENTAL TRAY

[76] Inventor: Michael Diesso, P.O. Box 648, Wareham, Mass. 02538

[21] Appl. No.: 739,879

[22] Filed: Aug. 2, 1991

[51] Int. Cl.⁵ .................................... A61C 9/00
[52] U.S. Cl. ....................................... 433/48; 433/214
[58] Field of Search .................... 433/37, 41, 48, 214; 128/861, 862

[56] References Cited

U.S. PATENT DOCUMENTS

| | | | |
|---|---|---|---|
| 5,011,407 | 4/1991 | Pelerin | 433/48 |
| 5,026,278 | 6/1991 | Oxman et al. | 433/41 |
| 5,040,976 | 8/1991 | Ubel, III et al. | 433/41 |
| 5,066,231 | 11/1991 | Oxman et al. | 433/214 |

Primary Examiner—Gene Mancene
Assistant Examiner—Cindy A. Cherichetti
Attorney, Agent, or Firm—Laff, Whitesel, Conte & Saret

[57] ABSTRACT

A custom dental tray is prepared by a dentist who manually works a soft dough-like composition of polycaprolactone polymer onto a stone dental cast and allows the polymer to harden to form the custom dental tray. The polycaprolactone polymer has an average molecular weight of from about 35,000 to about 60,000 and a crystalline melting point of from about 120° F. to about 160° F. and which is hard at temperatures of up to about 105° F.

7 Claims, 1 Drawing Sheet

CUSTOM DENTAL TRAY

BACKGROUND OF THE INVENTION

The present invention relates to a polycaprolactone custom dental tray and a method of making said tray.

A dental tray is a receptacle that is used to carry a material such as, impression, bleaching or fluoride, to the mouth. Its purpose is to confine the material in apposition to the surfaces of oral anatomy to be recorded or affected, and to control and confine that material while it sets or performs its function. There are two basic types—stock dental and custom dental trays. Stock dental trays are trays that have been prefabricated by a manufacturer in a variety of sizes that would closely approximate the anatomy of a wide grouping of people. They are available in standard sizes of small, medium and large. They are used only for preliminary procedures and produce preliminary gypsum models of the teeth and surrounding structures.

Custom dental trays are trays that are made by the dentist or dental laboratory on preliminary gypsum models and are designed to enable the dentist to make a more accurate and detailed impression, or treatment than is possible with stock trays. Custom dental trays are fabricated for a specific procedure, for one person, and are precisely made to that one person's individual oral anatomy. They are discarded after use.

One of the techniques used to fabricate custom dental trays is to first form a preliminary gypsum model with a stock dental tray. Preformed flat sheets of a shellac composition or a thermoplastic are placed on a gypsum model and heated to a soft, deformable, adaptable state. The softened sheet is then pressure formed to conform to the gypsum model. This method produces an excess of material overlapping the model and requires substantial finishing, grinding and polishing. The shellac material is also brittle when hardened and subject to fracture in the mouth when being used as a custom dental tray.

A variation of the above method is known from U.S. Pat. No. 4,401,616. In U.S. Pat. No. 4,401,616 a custom dental tray is made by using a thermoplastic flat uniform thickness sheet which is manually bent over the gypsum cast. The thermoplastic sheet is made of Polyform. The chemical make-up of Polyform was not disclosed. However, the use sheet material requires extensive trimming and cutting.

U.S. Pat. No. 4,569,342 teaches a variation of the above method. A stock tray is made of thermoplastic material i.e. methylmethacrylate, heated so as to soften, and then remanipulated and reshaped according to the biting surfaces of the patient. The tray requires extensive trimming.

The Tone polymer literature distributed by Union Carbide states that poly caprolactone polymers may be mixed with various polymers and may be utilized as orthopedic casts; plaster replacement; controlled release matrix; as an adhesive when combined with other polymers; a mold release characteristic when added to polycarbonate; poly (butylene terephthalate)—fiberglass and the like; a pigment dispersant; in biodegradable systems; shoe counters; do it yourself toy or hobby applications; and synthetic wound dressings. The Tone literature does not discuss nor suggest the use of polycaprolactone polymers for custom dental trays.

In all cases the current technology and materials available for the fabrication of custom dental trays are dependent upon a preformed-form of one sort or another that is readaptable or readjustable. This denies the dental professional the freedom of true individualized custom molding capabilities for each patient. Each of the prior art methods also produces an excess of material circumferencially around the periphery of the tray. This excess must be trimmed through grinding, shearing and polishing to prevent irritation and effectuate a correct fit. This is a time consuming and messy process. The present invention provides a method for making custom dental trays that is not dependent on or limited to the confines or restrictions of a preform. The present invention instead offers true freedom to the dentist of a wide and unlimited variety of geometric configurations to suit individual patients without limit to size or shape. Further, my method can even be used in veterinary dentistry. That is on the odd, difficult and differing shapes of equine, feline and canine oral anatomies.

My method for making custom dental trays substantially limits any excess over extensions of material at the periphery of the model and substantially reduces any trimming, grinding, shearing, polishing and smoothing. This saves time and expense to both patient and dentist.

Therefore it is an object of the present invention to provide a simplified method of preparing a custom dental tray by the dentist in his office.

It is another object of the present invention to provide a method of preparing a custom dental tray without utilizing extensive trimming, cutting and polishing of the custom dental tray.

It is another object of the present invention to provide a custom dental tray by placing a quantity of thermoplastic aggregate i.e. beads, pellets, powder or granules in a container of hot water which is at a temperature of about 140° F. to boiling; the thermoplastic material remains in the water until it forms a soft pliable conglomerate or non-descript mass of thermoplastic; the soft pliable thermoplastic mass is removed from the hot water; manually working the soft pliable thermoplastic into a pliable usable shape; covering only the teeth and/or gingiva of a dental cast, i.e. confined within the periphery; maintaining the thermoplastic on the cast until the thermoplastic hardens and cools to substantially room temperature; removing the hardened room temperature thermoplastic from the cast and submerging the room temperature cast in cold water having a temperature of from about 40° F. to about 60° F. for at least about 30 seconds to form a hardened custom dental tray.

Still another object of the present invention is to use an organic thermoplastic material to prepare the custom dental tray wherein the thermoplastic material contains at least about 75% by weight of a polycaprolactone of the formula

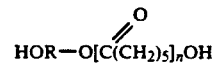

wherein R is an aliphatic group, and n is 300 to 650 and preferably has an average molecular weight of from about 35,000 to about 60,000 and a crystalline melting point of from about 120° F. to about 150° F.

Still another object of the present invention is to provide a polycaprolactone custom dental tray.

A still further object of the present invention is to provide a polycaprolactone custom dental tray wherein the polycaprolactone has the formula

wherein R is an aliphatic group, and n is 300 to 650 and preferably has a molecular weight of about 35,000 to about 60,000 and a crystalline melting point of from about 120° F. to about 160° F. and preferably from about 130° F. to about 150° F.

SUMMARY OF THE INVENTION

The invention is directed to a method of preparing a one-piece plastic custom dental tray in the dentists office and to a polycaprolactone custom dental tray. The preferred method of preparing a single custom dental tray is to place two to three tablespoons of polycaprolactone beads or pellets in a cup of hot water having a temperature of at least 160° F. (an instant type coffee machine produces a cup of hot water on demand). The polycaprolactone is preferably a mixture of polycaprolactones having an average molecular weight from about 35,000 to about 45,000 and having a preferred melting temperature of from about 130° F. to about 150° F. The beads remain in the hot water until they all melt and form a soft pliable conglomerate mass. Then the soft pliable mass is removed from the hot water and preferably manually rolled into a pencil type rod approximately the length of the arc of the custom dental tray. The rod may have an enlarged center portion. The soft pliable rod is placed on a dental cast and worked manually to cover only the teeth or gingiva. The enlarged central portion is stretched and manipulated to form an individualized handle. The warm thermoplastic is allowed to cool to approximately room temperature on the cast—i.e. from about 5 to about 10 minutes. The custom dental tray is removed from the cast and placed in cold water from about 30 seconds to about two minutes to form a hardened custom dental tray.

DESCRIPTION OF THE PREFERRED EMBODIMENT

Figure 2:
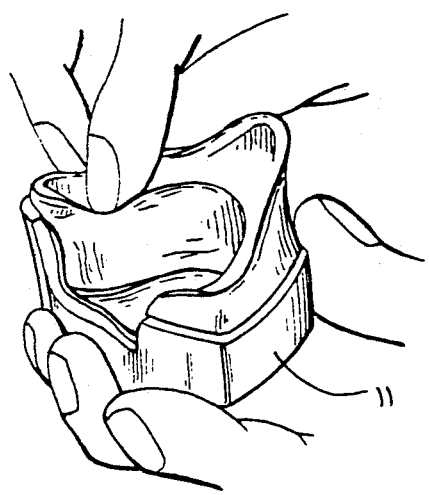
FIG. 2 is a perspective view of the roll of FIG. 1 shaped on a dental cast.
Figure 3:
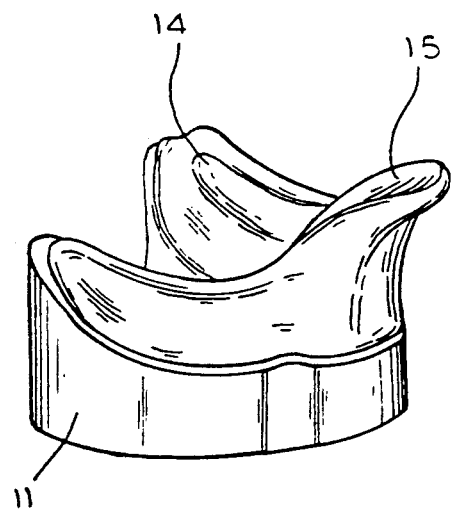
FIG. 3 is a perspective view of the roll of FIG. 1 shaped on the dental cast to form a custom dental tray.

When forming a custom dental tray for a patient a cast is first made of that portion of the patient's mouth to be treated. In the case of a full cast, an appropriate maxillary and/or mandibular cast is made. The cast 11 shown in FIGS. 2 and 3 is a mandibular cast and is preferably made of gypsum and is commonly referred to as a stone cast.

To form the custom dental tray of my invention, I take a measurable amount of a thermoplastic aggregate and place it into hot non-solvent neutral liquid, i.e. water. The aggregate is in the form of powder, granules, beads, pellets or fragments. To make a full mandibular custom dental tray for an average adult, the amount of aggregate used is generally about 1.5 to about 3 tablespoons. The amount of aggregate may be freely determined by the dentist to precisely match the extent of the individual custom dental tray to fabricated.

The water is heated to a temperature of from about 140° F. to about 180° F. This is conveniently done in the dentists office by an instant coffee maker. The aggregate, which is preferably pellets and/or beads remain in the water for a period of from about 30 seconds to two minutes. This allows the pellets and/or beads to congeal to a non-distinct bolus or ball like mass having a non-specific form and being in a semi-liquid plasma state. In this state the polymeric material is capable of assuming a multiplicity of geometric configurations and is not limited by size, shape or dimensional constraints.

Figure 1:
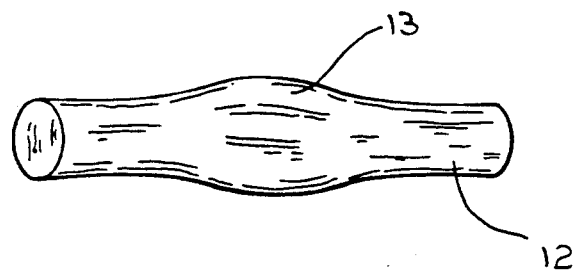
FIG. 1 is a perspective view of a roll of soft polymeric material used in the present invention.

The soft polymeric composition is removed from the hot water. It is dough-like and capable of free unrestricted manual manipulation. Preferably the soft dough-like polymeric composition is rolled to a pencil rod shape 12 as shown in FIG. 1. The dough-like rod 12 has an enlarged central portion 13. The length of the rod 12 is generally equal to the arc length of the cast 11 or whatever the custom dental tray is being made for. The soft rod 12 is then placed on top of the cast 12 and manipulated by the dentist to cover only the teeth and/or gingiva of the cast 12 as is illustrated in FIG. 2.

Generally, prior to placing the soft rod 12 on the cast 11, an aluminum foil spacer or other appropriate spacer (not shown) is placed on the mandibular cast 12 over the entire teeth area. Therefor the soft rod is placed on the spacer and then manually manipulated by the dentist to cover only the teeth portion of the cast.

Figure 4:
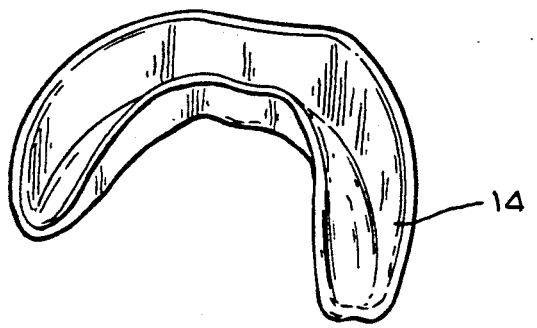
FIG. 4 is a perspective view of a custom dental tray of the present invention.

The custom dental tray 14 as shown in FIG. 4, is generally U-shaped. The enlarged center portion 13 of the rod is manipulated to form a handle 15 which protrudes forwardly from the tray 14. The handle is shaped by the dentist to have a comfortable fit for the individual dentist's thumb and forefinger. This is an advantage to the dentist who is doing the work. He is able to provide a tray which is a custom fit for the patient and is also a custom fit for him. This enables the dentist to work with more ease in performing his task with the custom dental tray.

As shown in FIG. 2, the soft polymeric composition is manually manipulated onto the mandibular cast to conform to the individual peculiarities of the mandibular cast to form the shape as shown in FIG. 3. The custom dental tray 14 as it sits on the mandibular cast 11 is allowed to cool to approximately room temperature. Preferably the custom dental tray is allowed to cool from about five minutes to about ten minutes in ambient air. Sufficient cooling is desired to allow the custom dental tray on the cast 11 to become sufficiently hard to allow it to be removed from the mandibular cast without changing the configuration of the dental tray from what it was on the cast.

After the dental tray is removed from the cast, it is placed in a container of cold water. The cold water has a temperature of from about 40° F. to about 60° F. The custom dental tray remains in the cold water from about 30 seconds to about three minutes to fully harden the custom dental tray. The custom dental tray can now be used on the patient for its intended purpose. If necessary adjustments can be made with the aid of a pinpoint torch or the like.

The preferred manner of preparing my custom dental tray is as stated above. However, for some cases, it may be desireable to hand custom the dental tray directly in the patient's mouth in order to precisely conform the dental tray to every detail of the patient's teeth anatomy. Care should be taken to mold only to the extent desired by the dentist to eliminate any over extensions of excess material that would require grinding and/or trimming. In approximately from about 5 to about 10 minutes the polymeric material hardens to a ridged non-deformable custom dental tray and can be removed from the patient's mouth. Preferably the dental tray is paced in the cold water bath described above to completely harden. Then the custom dental tray can now be used for the procedure required.

The thermoplastic polymer composition best suited for the method of preparing my custom dental tray is a homopolymer of caprolactone which is initiated with a diol. The is polycaprolactone polymer used in the present invention has the formula:

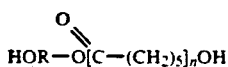

wherein R is an aliphatic hydrocarbon and n is 300 to 650.

The preferred average molecular weight of the polycaprolactone is from about 35,000 to about 60,000. The preferred caprolactone polymer is a mixture of 35 parts by volume of TONE P-700 and 65 parts by volume of TONE P-767. Both of these polymers are manufactured by Union Carbide Corporation, U.S.A. As previously stated, the preferred form is extruded pellets and/or beads or rods.

TONE P-700 and P-767 are described as homopolymers of $\epsilon$-caprolactone. The polymerization is initiated by a diol (HO—R—OH). The caprolactone is a seven-membered ring compound. TONE P-767 has an average molecular weight of approximately 43,000 and is prepared from a special high purity grade of caprolactone monomer. Typical properties of TONE P-767 are a tensile strength psi (MPa) of 3000-4500 (21.0 31.0); an elongation, % of 600-1,000; and a melting point (by DSC), of 55°-65° C.

TONE P-700 is semi-rigid at room temperature. The basic physical properties are shown in Table 1.

TABLE 1

| | |
|---|---|
| Tensile Modulus, psi (MPa) | 60,000 (414) |
| Yield Stress, psi (MPa) | 1,600 (11.0) |
| Tensile Strength, psi (MPa) | |
| 2 in/min | 4,500 (31.0) |
| 20 in/min | 4,000 (27.6) |
| Ultimate Elongation, % | |
| 2 in/min | 600 to 800 |
| 20 in/min | 600 to 800 |
| Flexural Modulus, psi (MPa) | 62,000 (428) |
| Flexural Stress at 5% Strain, psi (MPa) | 2,470 (17.1) |
| Notched Izod Impact Strength, $\frac{1}{8}$-in bar, ft-lb/in of notch (J/m) | 3 to 8 (160 to 425) |
| Unnotched Izod Impact Strength, $\frac{1}{8}$-in bar | No Break |
| Tensile Impact Strength, ft-lb/in (kJ/M) | 60 (126) |
| Density, p. g/cc at | |
| 0° C. (32° F.) | 1.160 |
| 20° C. (68° F.) | 1.149 |
| 40° C. (104° F.) | 1.134 |
| 60° C. (140° F.) | 1.070 |
| 90° C. (194° F.) | 1.050 |
| (Delta)p/(Delta)T at −30° C. to 30 C., g/cc·°C. | $-5.6 \times 10^{-4}$ |
| (Delta)p/DeltaT at 60° C. to 100° C., g/cc·°C. | $-6.8 \times 10^{-4}$ |
| Moisture content | |
| at 50% Relative Humidity, % | 0.07 |

TABLE 1-continued

| | |
|---|---|
| at 100% Relative Humidity, % | 0.43 |

Thermal properties of TONE Polymer P-700 are given in Table 2. The crystalline melting point is about 60° C. which is about 140° F.

TABLE 2

| | |
|---|---|
| $T_m$, Crystalline Melting Point[1], °C. (°F.) | 60 (140) |
| $T_g$, Amorphous, °C. (°F.) | −70 (−94) |
| $T_g$, Partially Crystalline, °C. (°F.) | −60 (−76) |
| Delta $H_f$, Heat of Fusion[1], two weeks at 23° C., cal/g | 18.5 |
| Delta $H_c$, Heat of Crystallization[2], cal/g | 14.6 |
| Delta $H_f$, Heat of Fusion[3], no annealing, cal/g | 14.7 |
| $T_c$[4], (cooling rate = 10° C./min), °C. | 20 |
| $T_c$[5], sec | |
| at 20° C. (68° F.) | 0.473 |
| at 40° C. (104° F.) | 0.659 |
| at 80° C. (176° F.) | 0.533 |
| at 100° C. (212° F.) | 0.545 |
| at 150° C. (302° F.) | 0.555 |

[1] Crystalline melting point $T_m$, and DeltaH$_f$ were determined on a sample two weeks after compression molding.
[2] Heat of crystallization of molten sample cooled at 10° C./min.
[3] Heat of fusion determined on the sample directly after crystallization.
[4] Temperature of maximum crystallization rate after cooling at 10° C./min from above $T_m$.
[5] Samples were heated to 100° C., cooled at 160° C./min to designated temperature; time to reach maximum crystallization rate, $T_c$, was determined.

Once the custom dental tray has been prepared, it can be readily utilized by the dentist for its intended purpose. After use it can be discarded. However, if for some reason the tray must be remade, it may be placed in hot water and returned to a non-distinct dough-like mass. The soft mass can then be reworked as previously set forth to form the desired custom dental tray.

The above detail description refers to a custom dental tray which is entirely made of polycaprolactone polymers. However, my invention is intended to cover those instances where a dentist decides to prepare a custom dental tray which is only made partially of polycaprolactone. My invention also includes altering or repairing a non-polycaprolactone custom dental tray with softened polycaprolactone polymers. For instance, if a non-polycaprolactone custom dental tray has already been made, the dentist can test the non-polycaprolactone custom dental tray to determine if it is compatable with polycaprolactone—i.e., if softened polycaprolactone custom dental tray so as be an intimate part thereof. If the polycaprolactone is compatible, then the softened polycaprolactone can be used to alter and/or repair the non-polycaprolactone custom dental tray to form the desired partial polycaprolactone custom dental tray.

The above preferred embodiment is not intended to limit the scope of the invention. Other modifications coming within the intended scope of the invention may be obvious to those skilled in the art.

I claim:

1. A custom dental tray comprising a polymer composition containing at least about 75% by weight of polycaprolactone polymers wherein said composition has melting point of from about 120° F. to about 160° F.; said polycaprolactone polymers have an average molecular weight of from about 35,000 to about 60,000, and said polycaprolactone polymers have the formula

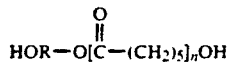

wherein R is an aliphatic group, and n is 300 to 650.

2. The custom dental tray of claim 1 wherein the polymer composition essentially consists of polycaprolactone polymers.

3. A custom dental tray which has a portion thereof prepared from a polymer composition which consists essentially of polycaprolactone polymers, said composition having a melting point of from about 120° F. to about 160° F., and said polycaprolactone polymers have the formula

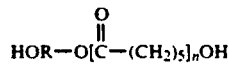

wherein R is an aliphatic group, and n is 300 to 650.

4. A method of preparing a custom dental tray comprising:

forming said custom dental tray from a non-sheet polymeric composition which has a melting point of from about 120° F. to about 160° F. and is hard at room temperature and body temperature, said polymers have an average molecular weight of from about 35,000 to about 60,000, and said polymer composition essentially consists of polycaprolactone polymers of the formula

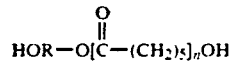

wherein R is an aliphatic hydrocarbon, and n is 300 to 650.

5. A method of preparing a custom dental tray comprising:

heating aggregate polymeric material in a non-solvent liquid to form a soft non-distinct mass, said non-solvent being at a temperature of at least about 140° F., said polymeric material comprising at least about 75% by weight of polycaprolactone polymers and having melting point of from about 120° F. to about 160° F. and is hard at room temperature and at body temperature, said polycaprolactone polymers have an average molecular weight of from about 35,000 to about 60,000;

removing said soft mass from said non-solvent liquid;

forming said soft mass into a workable soft mass;

placing said soft workable soft mass on a dental cast;

covering only a desired portion of said cast with said workable soft mass;

cooling said workable soft mass on said dental cast to form thereon a custom dental tray;

removing said custom dental tray from said cast; and cooling said removed custom dental tray to provide a hard custom dental tray.

6. The method of claim 5 wherein the polymer composition essentially consists of polycaprolactone polymers of the formula

wherein R is an aliphatic group, and n is 300 to 650.

7. The method of claim 6 wherein the non-solvent liquid is water and said aggregate is heated in hot water from about 30 seconds to about two minutes, said soft mass is worked into a soft rod-like form which is placed on the dental cast, manually working the soft rod-like form on the dental cast to cover substantially only the teeth of said cast; manually working a center portion of the mass to form a protruding handle; and cooling the custom dental cast in cold water for at least one minute and said cold water having a temperature of from 40° F. to 60° F.

* * * * *